United States Patent
Dubovoy et al.

(10) Patent No.: US 9,861,562 B2
(45) Date of Patent: Jan. 9, 2018

(54) OCCLUSIVE PERSONAL CARE COMPOSITION

(71) Applicant: COLGATE-PALMOLIVE COMPANY, New York, NY (US)

(72) Inventors: Viktor Dubovoy, Cresskill, NJ (US); Michael Stranick, Bridgewater, NJ (US); Peter R. Hilliard, Jr., Far Hills, NJ (US); Laurence Du-Thumm, Princeton, NJ (US); Long Pan, Somerset, NJ (US)

(73) Assignee: COLGATE-PALMOLIVE COMPANY, New York, NY (US)

( * ) Notice: Subject to any disclaimer, the term of this patent is extended or adjusted under 35 U.S.C. 154(b) by 0 days.

(21) Appl. No.: 14/971,448

(22) Filed: Dec. 16, 2015

(65) Prior Publication Data

US 2017/0172868 A1 Jun. 22, 2017

(51) Int. Cl.
*A61K 8/24* (2006.01)
*A61K 8/88* (2006.01)
*A61Q 15/00* (2006.01)

(52) U.S. Cl.
CPC .................. *A61K 8/24* (2013.01); *A61K 8/88* (2013.01); *A61Q 15/00* (2013.01); *A61K 2800/30* (2013.01); *A61K 2800/596* (2013.01)

(58) Field of Classification Search
CPC .......... A61K 2800/30; A61K 2800/596; A61K 8/24; A61K 8/88; A61Q 15/00
See application file for complete search history.

(56) References Cited

U.S. PATENT DOCUMENTS

| | | | |
|---|---|---|---|
| 6,090,773 A * | 7/2000 | Lukenbach | A61K 8/44 510/119 |
| 6,706,679 B1 * | 3/2004 | Bergeron | A61K 8/046 348/E5.028 |
| 7,537,752 B2 * | 5/2009 | De Lacharriere | A61K 8/44 424/401 |
| 2004/0126411 A1 * | 7/2004 | Lagatol | A61K 8/0208 424/443 |
| 2010/0120923 A1 * | 5/2010 | Stewart | A61L 24/0015 514/772.1 |
| 2012/0021025 A1 | 1/2012 | Bendejacq et al. | |
| 2015/0306008 A1 | 10/2015 | Yuan et al. | |

FOREIGN PATENT DOCUMENTS

| WO | WO02074271 | 9/2002 |
|---|---|---|
| WO | WO2013013903 | 1/2013 |

OTHER PUBLICATIONS

Shao et al. (Molecular Bioscience, 2009, pp. 464-471).*
Lanigan (International Journal of Toxicology, Published 2001, pp. 75-89).*
Detergent Builders (http://www.detergentsandsoaps.com/detergent-builders.html, pp. 1-3, accessed on May 9, 2017).*
Ashland; "N-DurHance™ A-1000 conditioning polymer"; Product Data, 2014.
Hossel et al., "Conditioning polymers in today's shampoo formulations—efficacy, mechanism and test methods," International Journal of Cosmetic Science (2000) 22, 1-10.
Cin et al. 'Polyphosphates asinorganic polyelectrolytes interacting with oppositely charged ions, polymers and deposited on surfaces: fundamentals and applicants', Advances in Colloid and Interface Science. 2014, vol. 209, p. 89, col. 1-2.

\* cited by examiner

*Primary Examiner* — Alma Pipic

(57) ABSTRACT

Described herein, are compositions comprising a soluble quaternary ammonium polymer/polyphosphate complex made by combining ingredients comprising a quaternary ammonium polymer and polyphosphates having 2 or more phosphate units. Methods of making and using these compositions are also described.

20 Claims, No Drawings

OCCLUSIVE PERSONAL CARE COMPOSITION

BACKGROUND

There have been many antiperspirants designed to help people reduce sweat. Examples of these can be found in U.S. Code of Regulation 21 C.F.R. §350. The majority of the active agents used in antiperspirants are aluminum and zirconium halide compounds and complexes and their derivatives. While generally effective, some of these compounds are acidic and can stain clothes, among other things. Thus, there is a need for alternative antiperspirant actives. Embodiments of the present invention are designed to meet this need.

SUMMARY

An embodiment of the present disclosure is directed to a personal care composition comprising: a soluble quaternary ammonium polymer/polyphosphate complex. The complex can be formed by combining in a composition at least one polyphosphate compound having 2 or more phosphate units and at least one quaternary ammonium polymer. In one embodiment, the quaternary ammonium polymer is polyacrylamidopropyltrimonium chloride.

In another aspect, the present disclosure provides a method of occluding pores of a subject comprising applying a personal care composition comprising at least one polyphosphate compound having 2 or more phosphate units and at least one quaternary ammonium polymer to the skin of the subject.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

In one embodiment, the present disclosure provides a soluble quaternary ammonium polymer/polyphosphate complex. The complex may be made by combining in a composition at least one polyphosphate compound having 2 or more phosphate units and at least one quaternary ammonium polymer. These ingredients may be combined to form a pre-formed complex, which could be prepared in bulk, and then incorporated into personal care compositions. Such a combination may occurs in a suitable solvent, such as an aqueous solvent or non-aqueous solvent (e.g., hydrophilic or hydrophobic). Alternatively, these ingredients may be combined during the manufacture of a personal care composition, in order to form the complex in-situ. The combining of the materials can be in an aqueous solvent.

In one embodiment, the quaternary ammonium polymer is a poly(N-(trialkylaminoalkyl)acrylamide), for example, $[CH_2CHCONHR]_n$, wherein R is a quaternary ammonium trialkylaminoalkyl group. Such trialkyl aminoalkyl groups are of the general formula $(alkylene)N^+(alkyl)_3X^-$, wherein X is a counterion to the quaternary ammonium ion. "Alkylene" may be a C2-10 straight or branched chain alkyl moiety, while "alkyl" may be a C1-8 straight or branched chain alkyl moiety. "X" may be any suitable anion, such as fluoride, chloride, bromide, sulfate, phosphate, and the like. Such group include, for example, trimethylaminoethyl, trimethylaminopropyl, triethylaminoethyl, triethylaminopropyl, trimethylaminobutyl, triethylaminnobutyl, and the like. In one embodiment, the trialkyl aminoalkyl group is trimethylaminopropyl, e.g., trimethylaminopropyl chloride. Such polymer is commonly known as polyacrylamidopropyltrimonium chloride. The polyacrylamidopropyltrimonium chloride can be purchased as N-Durance A1000 from Ashland Chemical. In one embodiment, the number average molecular weight is 100,000 to 500,000 daltons, 200,000 to 400,000 daltons, or about 300,000 daltons.

Any polyphosphate having 2 or more phosphate units can be employed as the at least one polyphosphate, in any salt form. In one embodiment, the polyphosphate comprises a tripolyphosphate, such as sodium tripolyphosphate or potassium tripolyphosphate, or a diphosphate (pyrophosphate), such as tetrasodium pyrophosphate or tetrapotassium pyrophosphate. In another embodiment, the polyphosphate may comprises polyphosphates having 4 or more or 6 or more phosphate units. In a particular embodiment, the polyphosphate comprises a long chain polyphosphate having 6 to 50 phosphate units, e.g., 6 to 30 phosphate units, 10-30 phosphate units or 20-30 phosphate units. One such polyphosphate is sodium hexametaphosphate, which is a 6-phosphate cyclic molecule of the formula $(NaPO_3)_6$. Linear 6-phosphate polyphosphate may also be used. The polyphosphate used herein may be either linear, cyclic or mixtures of both forms. The counter ion for the polyphosphate can be any suitable cation. Examples include, but are not limited to, sodium, potassium, calcium, magnesium, ammonium, zinc and the like. Particular examples of long-chain polyphosphates include those having an average of 6, 9, 11, 12, 13, 15, 17, 18, 19, 21, 23, 24 or 25 phosphate units. A preferred polyphosphate is a polyphosphate having an average length of 20-25 phosphate units, e.g., 23 phosphate units. In one embodiment, the polyphosphate comprises a sodium polyphosphate having an average length of 20-25 phosphate units, e.g., 23 phosphate units. Such a polymer is often referred to as "sodium hexametaphosphate, long chain,"and has also been referred to as sodium polyphosphate, sodium polymetaphosphate, glassy sodium polyphosphate, glassy sodium phosphate, Glass H and Vitrafos. This polyphosphate typically has a $P_2O_5$ content of 68-71 wt %, e.g., about 69 wt %. To avoid confusion, as used herein below, the term "sodium polymetaphosphate" or "SPMP" refers to a sodium polyphosphate of average chain length 20-25 phosphate units, e.g., 23 phosphate units, either linear, cyclic or a mixture. Likewise, the term "polymetaphosphate" refers to a polyphosphate of average chain length of 20-25 phosphate units, e.g. 23 phosphate units, either linear, cyclic or a mixture.

The phosphorus to polymer ratio can be any ratio that results in a soluble complex at the desired pH in an aqueous solution. In some embodiments, the ratio of polyphosphate to polymer is from 1:2 to 50:1, by weight, for example, 1:1 to 10:1, or 1:1 to 9:1, or 1:1 to 8:1, or 2:1 to 8:1, or 2:1 to 6:1, or 2:1 to 5:1, or 2:1 to 4:1, or 2:1 to 3:1, or 10:1 to 50:1, or 10:1 to 40:1 or 10:1 to 25:1 or 10:1 to 25:1, or 12:1 to 24:1, or 16:1 to 20:1, or about 2:1, or about 2.5:1 or about 3:1, or about 12:1 or about 16:1 or about 20:1, by weight.

The compositions of the present disclosure can be included in a personal care composition. Examples of such compositions include, but are not limited to, antiperspirants, deodorants, body washes, shower gels, bar soaps, shampoo, hair conditioners and cosmetics.

For antiperspirant and/or deodorant compositions, the carrier can be any carrier that is used for antiperspirants and/or deodorants. The carrier can be in the form of a stick, a gel, a roll-on, or an aerosol (e.g. spray). For stick formulations, the carrier may include oils and/or silicones and gelling agents.

In an embodiment, the personal care compositions, such as antiperspirants and/or deodorants, include the soluble quaternary ammonium polymer/polyphosphate complex made by made by combining in the composition at least one quaternary ammonium polymer and at least one polyphosphate having 2 or more phosphate units. These ingredients may be combined to form a pre-formed complex, which could be prepared in bulk, and then incorporated into personal care compositions. Such a combination may occurs in a suitable solvent, such as an aqueous solvent or non-aqueous solvent (e.g., hydrophilic or hydrophobic). Alternatively, these ingredients may be combined during the manufacture of a personal care composition, in order to form the complex in-situ. The combining of the materials can be in an aqueous solvent.

In an embodiment, the complex can also be used to enhance the efficacy of other antiperspirant salts comprising a polyvalent cation, for example antiperspirant complexes of (i) aluminum and optionally zirconium, (ii) chlorohydrate, and (iii) optionally an amino acid and/or ammonium acid, for example glycine and/or trimethylglycine, e.g., aluminum zirconium tetrachlorohydrex glycine. In an embodiment, these other antiperspirant salts can be added to the formulations of the present disclosure in addition to the quaternary ammonium polymer polyphosphate complex. In an alternative embodiment, the formulation includes only very small amounts or is entirely or substantially free of the above aluminum or zirconium antiperspirant active complexes. For example, the formulations can include less than 2 weight %, or less than 0.5 weight %, or less than 0.1 weight %, or less than 0.01 weight %, or less than 0.001 weight % or less than 0.0001 weight % aluminum or zirconium, relative to the total weight of the formulation.

The present disclosure provides antiperspirant products comprising as an antiperspirant active a complex of a quaternary ammonium polymer (such as polyacrylamidopropyltrimonium chloride) with a polyphosphate, e.g., any of the quaternary ammonium polymer (such as polyacrylamidopropyltrimonium chloride)/polyphosphate complexes discussed herein, as well as methods of making and using such products. The present disclosure further provides methods of reducing sweat comprising applying the composition to skin, and methods of killing bacteria comprising contacting the bacteria with the composition.

In one embodiment, the present disclosure provides a composition (Composition 1), comprising at least one quaternary ammonium polymer and at least one polyphosphate having 2 or more phosphate units. In further embodiments, the present disclosure provides:

1.1 Composition 1, wherein the least one quaternary ammonium polymer and at least one polyphosphate having 2 or more phosphate units form a soluble complex.
1.2 Composition 1 or 1.1, wherein the quaternary ammonium polymer is a poly (N-trialkylaminoalkyl)acrylamide.
1.3 Any preceding composition, wherein the quaternary ammonium polymer is polyacrylamidopropyltrimonium chloride.
1.4 Any preceding composition, wherein the polyacrylamidopropyltrimonium chloride has a number average molecular weight 100,000 to 500,000 daltons, optionally 200,000 to 400,000 daltons, or about 300,000 daltons.
1.5 Any preceding composition, wherein the composition is in an aqueous solvent.
1.6 Any preceding composition, wherein the polyphosphate has 3 or more phosphate units, e.g., 4 or more phosphate units, or 6 or more phosphate units.
1.7 Any preceding composition, wherein the polyphosphate has from 6 to 50 phosphate units, e.g., 6 to 30 phosphate units, or 10 to 20 phosphate units, or about 23 phosphate units.
1.8 Any preceding composition, wherein the polyphosphate comprises sodium tripolyphosphate.
1.9 Any preceding composition, wherein the polyphosphate comprises a long-chain polyphosphate, e.g., a polyphosphate having an average of 6, 9, 11, 12, 13, 15, 17, 18, 19, 21, 23, 24 or 25 phosphate units.
1.10 Any preceding composition, wherein the polyphosphate comprises a long-chain polyphosphate having an average length of 20-25 phosphate units, e.g., about 23 phosphate units.
1.11 Any preceding composition, wherein the polyphosphate has a $P_2O_5$ content of 68-71 wt %, e.g., about 69 wt %.
1.12 Any preceding composition, wherein the polyphosphate comprises sodium polymetaphosphate.
1.13 Any preceding composition, wherein the ratio of polyphosphate to polymer is from 1:2 to 50:1, by weight, for example, 1:1 to 10:1, or 1:1 to 9:1, or 1:1 to 8:1, or 2:1 to 8:1, or 2:1 to 6:1, or 2:1 to 5:1, or 2:1 to 4:1, or 2:1 to 3:1, or 10:1 to 50:1, or 10:1 to 40:1 or 10:1 to 25:1 or 10:1 to 25:1, or 12:1 to 24:1, or 16:1 to 20:1, or about 2:1, or about 2.5:1 or about 3:1, or about 12:1 or about 16:1 or about 20:1, by weight.
1.14 Any preceding composition, wherein the composition comprises from 1-50 wt % of polyphosphate, by weight of the composition, e.g., from 1-40%, from 1-30%, from 2-20%, from 2-10%, from 5-40%, from 5-30%, from 5-20%, from 10-50%, from 10-40%, from 10-30%, from 10-20%, from 20-50%, from 20-40%, from 20-30%, from 30-50%, from 30-40%, or from 5-10%, or from 1-10%, or from 1-5% polyphosphate, by weight of the composition.
1.15 Any preceding composition, wherein the composition is a personal care composition, optionally, at least one of an antiperspirant or a deodorant.
1.16 Any preceding composition, wherein the composition is substantially free of aluminum complexes, or is substantially free of zirconium complexes, or is substantially free of both aluminum and zirconium complexes.
1.17 Any preceding composition, wherein a solution of the composition forms a precipitate upon dilution with water.
1.18 A method of occluding the pores of a subject comprising applying any composition described herein, e.g., Composition 1 or any of 1.1-1.12, e.g., wherein the composition is a personal care composition, to the skin of the subject.

1.19 The use of the any composition described herein, e.g., Composition 1 or any of 1.1-1.12, for the occlusion of the pores of a subject.
1.20 The use of a soluble complex comprising at least one quaternary ammonium polymer and at least one polyphosphate having 2 or more phosphate units for the occlusion of the pores of a subject.
1.21 Use 1.15, wherein the complex precipitates out of aqueous solution to occlude the pores.

Optional ingredients that can be included in an antiperspirant and/or deodorant formulation of the compositions of the present disclosure include solvents; water-soluble alcohols such as $C_{2-8}$ alcohols including ethanol; glycols including propylene glycol, dipropylene glycol, tripropylene glycol and mixtures thereof; glycerides including mono-, di- and triglycerides; medium to long chain organic acids, alcohols and esters; surfactants including emulsifying and dispersing agents; amino acids including glycine; structurants including thickeners and gelling agents, for example polymers, silicates and silicon dioxide; emollients; fragrances; and colorants including dyes and pigments. If desired, an antiperspirant and/or deodorant agent additional to the soluble quaternary ammonium polymer polyphosphate complex can be included.

The antiperspirant compositions can be formulated into topical antiperspirant and/or deodorant formulations suitable for application to skin, illustratively a stick, a gel, a cream, a roll-on, a soft solid, a powder, a liquid, an emulsion, a suspension, a dispersion or a spray. The composition can comprise a single phase or can be a multi-phase system, for example a system comprising a polar phase and an oil phase, optionally in the form of a stable emulsion. The composition can be liquid, semi-solid or solid. The antiperspirant and/or deodorant formulation can be provided in any suitable container such as an aerosol can, tube or container with a porous cap, roll-on container, bottle, container with an open end, etc.

The compositions can be used in a method to reduce sweating by applying the composition to skin. In certain embodiments, the application is to axilla. Thus the present disclosure provides a method for controlling perspiration comprising applying to skin an antiperspirant effective amount of a formulation of any embodiment embraced or specifically described herein.

The present invention is further illustrated through the following non-limiting example(s).

EXAMPLES

Example 1

Sodium tripolyphosphate (STPP) is prepared as 10% and 15% by weight solutions in deionized water. These solutions are mixed in a 1:1:1 weight ratio with polyacrylamidopropyltrimonium chloride solution (provided as a 20% active solution as N-Durance 1000 from Ashland Chemical with a weight average molecular weight of about 300,000) and deionized water. To avoid precipitating too early, the polymer solution is added last to the mixture. If added earlier, the low concentration of the polymer in the STPP/water solution will cause the polymer to precipitate out. In this example, the STPP is added to the polymer and then the water is added. This results in clear solutions. The prepared solutions are shown in Table 1 below.

TABLE 1

| Example No. | Mass STPP solution (g) | Mass Water (g) | Mass 20% polymer solution (g) | Final % STPP | Final % polymer | pH after prep. |
|---|---|---|---|---|---|---|
| 15% STPP, 20% polymer water | 7 | 7.3 | 7 | 4.92 | 6.6 | 7.93 |
| 10% STPP, 20% polymer water | 7.1 | 7 | 7 | 3.37 | 6.6 | 7.84 |

The solutions are clear.

Example 2

The solutions from Example 1 are diluted 2×, 4×, 8×, 16×, and 32× with deionized water. After dilution, percent transmittance of the samples is measured on a Turbiscan instrument. For the 15% STPP solution, the 8×, 16×, and 32× dilutions show immediate precipitation with about 2% transmittance. In contrast, the 2× and 4× dilutions show some initial precipitation with about 65% transmittance. For the 10% STPP solution, results are similar: the 8×, 16×, and 32× dilutions show immediate precipitation with about 2% transmittance, and the 2× and 4× dilutions show some precipitation with about 65-67% transmittance. The pH of the solutions 30 minutes after dilution is also measured. The results are shown in Table 2 below.

TABLE 2

| Dilution | pH of 15% solution | pH of 10% solution |
|---|---|---|
| 2× | 8.21 | 8.1 |
| 4× | 8.43 | 8.33 |
| 8× | 8.63 | 8.45 |
| 16× | 8.78 | 8.6 |
| 32× | 8.85 | 8.61 |

Example 3

Examples 1 and 2 are repeated with a lower concentration of polymer by using a 2.5 weight % solution of polyacrylamidopropyltrimonium chloride, instead of the 20 weight % solution in Example 1 and the elimination of the additional water. The STPP and polymer solutions are mixed at a 1:1 weight ratio. The prepared solutions are shown in Table 3 below.

TABLE 3

| Example No. | Mass STPP solution (g) | Mass 2.5% polymer solution (g) | Final % STPP | Final % polymer | pH after prep. |
|---|---|---|---|---|---|
| 15% STPP, 2.5% polymer water | 10 | 10 | 7.3 | 1.25 | 8.54 |
| 10% STPP, 2.5% polymer water | 10 | 10 | 5 | 1.25 | 8.75 |

The solutions are clear. The solutions are diluted 2×, 4×, 8×, 16×, and 32× with deionized water. After dilution, percent transmittance of the samples is measured on a Turbiscan instrument. For the 15% STPP solution, the 8×, 16×, and 32× dilutions again show immediate precipitation. For the 10% STPP solution, the results are similar: the 4×, 8×, 16×, and 32× dilutions show immediate precipitation.

Comparative Example 1

Solutions of 15% STPP, 10% STPP, 2.5% polymer, and 1.25% polymer are prepared. The samples are diluted 2×, 4×, 8×, 16×, and 32× with deionized water. All samples remain clear after dilution. This shows that a complex is formed between the polymer and the polyphosphate.

Example 4

Sodium polymetaphosphate (SPMP) solutions are prepared as 10%, 20%, 40%, 50%, and 60% by weight solutions in deionized water. These solutions are mixed in a 1:1:1 weight ratio with polyacrylamidopropyltrimonium chloride solution (provided as a 20% active solution) and deionized water. To avoid precipitating too early, the polymer solution is added last to the mixture. If added earlier, the low concentration of the polymer in the SPMP/water solution will cause the polymer to precipitate out. In this example, the SPMP is added to the polymer and then the water is added. This results in clear solutions. The prepared solutions are shown in Table 4 below.

TABLE 4

| Example No. | Mass SPMP solution (g) | Mass Water (g) | Mass 20% polymer solution (g) | Final % SPMP | Final % polymer | pH after prep. |
|---|---|---|---|---|---|---|
| 60% SPMP, 20% polymer water | 11.8 | 11.8 | 11.8 | 19.9 | 6.7 | 4.69 |
| 50% SPMP, 20% polymer water | 16 | 16 | 16 | 16.7 | 6.7 | 4.67 |
| 40% SPMP, 20% polymer water | 16 | 16 | 16 | 13.3 | 6.7 | 4.63 |
| 20% SPMP, 20% polymer water | 16 | 16 | 16 | — | 6.7 | 4.47 |
| 10% SPMP, 20% polymer water | 16 | 16 | 16 | — | 6.7 | 4.32 |

The 40%, 50%, and 60% solutions as prepared are clear, but a precipitate is present during formation of the 10% and 20% solutions.

Example 5

The 40%, 50%, and 60% solutions from Example 4 are diluted 2×, 4×, 8×, and 16× with deionized water. After dilution, percent transmittance of the samples is measured on a Turbiscan instrument. For the 40% solution, all dilutions show immediate precipitation with about 4-7% transmittance. For the 50% solution, all dilutions show immediate precipitation with about 2-7% transmittance. For the 60% solution, all dilutions show immediate precipitation with about 3-5% transmittance. The pH of the solutions 30 minutes after dilution is also measured. The results are in Table 5 below.

TABLE 5

| Dilution | pH of 40% solution | pH of 50% solution | pH of 50% solution |
|---|---|---|---|
| 2× | 4.76 | 4.76 | 4.84 |
| 4× | 4.95 | 5 | 5.05 |
| 8× | 5.16 | 5.21 | 5.29 |
| 16× | 5.42 | 5.42 | 5.55 |

Example 6

Since perspiration is typically slightly acidic, it is important that the precipitates that form do not redissolve under acidic conditions. The 2×, 4×, 8×, and 16× dilutions of the 40%, 50%, and 60% SPMP solutions are tested for acid resistance. All solutions were treated with acid to lower the pH to about 1.5. It is found that the precipitate in each sample remained substantially undissolved at the lower pH.

Example 7

Examples 4 and 5 are repeated using the 2.5 weight % solution of polymer, instead of the 20 weight % solution of polymer used in Example 4, and the elimination of the additional water. The SPMP and polymer solutions were mixed at 1:1 weight ratio. The prepared solutions are shown in Table 6 below.

TABLE 6

| Example No. | Mass SPMP solution (g) | Mass 2.5% polymer solution (g) | Final % SPMP | Final % polymer | pH after prep. |
|---|---|---|---|---|---|
| 60% SPMP, 2.5% polymer | 10 | 10 | 30 | 1.25 | 4.69 |
| 50% SPMP, 2.5 polymer | 10 | 10 | 25 | 1.25 | 4.82 |
| 40% SPMP, 2.5% polymer | 10 | 10 | 20 | 1.25 | 4.93 |
| 30% SPMP, 2.5% polymer | 10 | 10 | 15 | 1.25 | 5.04 |
| 20% SPMP, 2.5% polymer | 10 | 10 | Turbid | | |
| 10% SPMP, 2.5% polymer | 10 | 10 | | | |

The 30%, 40%, 50%, and 60% solutions as prepared are clear, but a precipitate is present during formation of the 10% and 20% solutions.

The solutions are diluted 2× and 4× with deionized water. For the 2× dilution, the 30% and 40% solutions show immediate precipitation, but the 50% and 60% solutions do not. For the 4× dilution, all samples show immediate precipitation.

Example 8

The SPMP/polyacrylamidopropyltrimonium chloride complex precipitate is analyzed with X-ray Photoelectric Spectroscopy by depositing the precipitate on a Silicon wafer and allowing the precipitate to dry into a film. The results are shown in Table 7 below.

TABLE 7

| Material | Atomic Percent | | | | | |
|---|---|---|---|---|---|---|
|  | C | O | N | N$^+$ | Na | P |
| SPMP |  | 59.8 |  |  | 21.87 | 18.33 |
| Poly-acrylamidopropyltrimonium chloride | 75 | 11.43 | 7.36 | 6.21 |  |  |
| Precipitate | 44.9 | 31.39 | 4.4 | 4.13 | 6.08 | 9.1 |

The analysis of the SPMP/polymer thin film precipitate reveals that all of the elements contained in both starting materials are present in the precipitate. This suggests that the precipitate is a combination of SPMP and polymer. The O/P ratio is slightly higher in the precipitate than in SPMP due to the additional oxygen from the polymer. The Na/P ratio is lower than that for SPMP, indicating a deficiency in sodium in the precipitate relative to SPMP. The ratio of (N$^+$+Na)/P is the same as that for the SPMP reference, indicating that the N$^+$ from the polymer is substituting for Na in SPMP, which is theorized to constitute a bonding between the starting materials that forms the precipitate. The P/N$^+$ ratio can be used to approximate the stoichiometry for the precipitate, since N$^+$ is unique to the polymer while P is unique to the SPMP. This ratio indicates that for each SPMP unit of 25 P atoms that there are approximately 11 N$^+$ atoms. Thus the precipitate is composed of approximately 11 polymer monomer units for each SPMP unit. About half the Na atoms in the SPMP are replaced by N$^+$ from the polymer. The calculated composition for the 1 SPMP:11 monomer structure is near to that for the actual precipitate. This suggests that the proposed stoichiometry for the precipitate approximates that for the actual precipitate.

Example 9

Three aqueous solutions of SPMP are prepared: 10% SPMP, 20% SPMP, and 30% SPMP. Additionally, two solutions of polyacrylamidopropyltrimonium chloride are prepared: 2.5% polymer, and 1.25% polymer. All of these solutions remain clear after formation. The 10% SPMP and the 1.25% polymer solutions are each diluted 2× and 4× with deionized water and aged for three weeks. All dilutions remain clear after aging. This shows that the formation of a precipitate is unique to the combination of the polymer and the phosphate in the same solution, thus suggesting that a complex is formed between them that is responsible for the precipitation.

The above examples show that the polyphosphate/polymer complex can precipitate when diluted. When applied to skin, perspiration can cause the complex to form a precipitate, which can then occlude pores.

Example 10

A typical roll-on antiperspirant formulation comprising the polyphosphate/polymer complex of the present disclosure can be formulated as described in Table 8 below:

TABLE 8

| Material | Weight Percent |
|---|---|
| Polyphosphate/polymer complex | 5-30% |
| Steareth-20 | 1-10%, e.g., 2% |
| PPG-15 Stearyl Ether | 1-10%, e.g, 2% |
| Steareth-2 | 1-15%, e.g., 3% |
| Cyclomethicone | 1-10%, e.g., 2% |
| Fragrance | 0.5-5%, e.g, 1% |
| Water | Q.S. |

The invention claimed is:

1. A personal care composition, comprising:
   a soluble quaternary ammonium polymer polyphosphate complex formed by combining:
   at least one quaternary ammonium polymer; and
   at least one polyphosphate having 2 or more phosphate units; and
   a solvent;
   wherein the personal care composition is at least one of an antiperspirant or a deodorant, and
   wherein the personal care composition comprises from 20% to 50% by weight of the at least one polyphosphate.

2. The personal care composition of claim 1, wherein the at least one quaternary ammonium polymer is a poly(N-trialkylaminoalkyl)acrylamide.

3. The personal care composition of claim 1, wherein the at least one quaternary ammonium polymer is polyacrylamidopropyltrimonium chloride.

4. The personal care composition of claim 3, wherein the polyacrylamidopropyltrimonium chloride has a number average molecular weight greater than or equal to 100,000 daltons and less than or equal to 500,000 daltons.

5. The personal care composition of claim 1, wherein the solvent is an aqueous solvent.

6. The personal care composition of claim 1, wherein the at least one polyphosphate has 3 or more phosphate units.

7. The personal care composition of claim 6, wherein the at least one polyphosphate has greater than or equal to 6 phosphate units and less than or equal to 50 phosphate units.

8. The personal care composition of claim 1, wherein the at least one polyphosphate comprises sodium tripolyphosphate.

9. The personal care composition of claim 1, wherein the at least one polyphosphate comprises sodium polymetaphosphate.

10. The personal care composition of claim 1, wherein the personal care composition is substantially free of aluminum complexes, or is substantially free of zirconium complexes, or is substantially free of both aluminum and zirconium complexes.

11. A method of occluding pores of a subject, the method comprising:
   applying the personal care composition of claim 1 to skin of the subject.

12. The personal care composition of claim 6, wherein the at least one polyphosphate has about 23 phosphate units.

13. The personal care composition of claim 1, wherein the at least one quaternary ammonium polymer is a poly(N-trialkylaminoalkyl)acrylamide, and
   wherein the at least one polyphosphate has greater than or equal to 6 phosphate units and less than or equal to 50 phosphate units.

14. The personal care composition of claim 13, wherein the at least one quaternary ammonium polymer is polyacrylamidopropyltrimonium chloride.

15. The personal care composition of claim 13, wherein the at least one polyphosphate comprises sodium polymetaphosphate.

16. The personal care composition of claim 14, wherein the at least one polyphosphate comprises sodium polymetaphosphate.

17. The personal care composition of claim 1, wherein the solvent is a non-aqueous solvent.

18. A personal care composition, comprising:
   a soluble quaternary ammonium polymer polyphosphate complex formed by combining in a solvent:
     at least one quaternary ammonium polymer; and
     at least one polyphosphate having 2 or more phosphate units;
   wherein the personal care composition comprises from 20% to 50% by weight of the at least one polyphosphate, and
   wherein the personal care composition is a cosmetic.

19. The personal care composition of claim 18, wherein the solvent is an aqueous solvent.

20. The personal care composition of claim 1, wherein the antiperspirant or deodorant further comprises a carrier in the form of a stick, a gel, a roll on, or an aerosol.

* * * * *